United States Patent
Harms et al.

(10) Patent No.: US 9,182,000 B2
(45) Date of Patent: Nov. 10, 2015

(54) SPRING ELEMENT FOR A DRUG DELIVERY DEVICE, USE THEREOF AND DRUG DELIVERY DEVICE

(75) Inventors: Michael Harms, Frankfurt am Main (DE); Steffen Raab, Frankfurt am Main (DE); Uwe Dasbach, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 381 days.

(21) Appl. No.: 13/258,154

(22) PCT Filed: Mar. 31, 2010

(86) PCT No.: PCT/EP2010/054339
§ 371 (c)(1),
(2), (4) Date: Dec. 6, 2011

(87) PCT Pub. No.: WO2010/112559
PCT Pub. Date: Oct. 7, 2010

(65) Prior Publication Data
US 2012/0089099 A1    Apr. 12, 2012

Related U.S. Application Data

(60) Provisional application No. 61/168,980, filed on Apr. 14, 2009.

(30) Foreign Application Priority Data

Mar. 31, 2009 (EP) .................................. 09004663

(51) Int. Cl.
*F16F 1/12* (2006.01)
*A61M 5/20* (2006.01)
*A61M 5/24* (2006.01)

(52) U.S. Cl.
CPC .................. *F16F 1/122* (2013.01); *A61M 5/20* (2013.01); *A61M 5/24* (2013.01)

(58) Field of Classification Search
USPC .......... 267/179, 180, 174, 166, 167, 178, 170
See application file for complete search history.

(56) References Cited

U.S. PATENT DOCUMENTS

| | | | |
|---|---|---|---|
| 3,198,508 A |   | 8/1965 | Melton et al. |
| 3,286,960 A | * | 11/1966 | Douglas et al. ................ 267/180 |
| 3,336,842 A | * | 8/1967 | Adelt ............................. 267/180 |
| 4,930,605 A | * | 6/1990 | Boyer et al. ................... 267/179 |

(Continued)

FOREIGN PATENT DOCUMENTS

JP        10-267062       10/1998

OTHER PUBLICATIONS

European Search Report for EP Application No. 09004663, dated Jul. 21, 2009.
International Search Report for PCT Patent Application No. PCT/EP2010/054339, dated Jun. 29, 2010.
(Continued)

*Primary Examiner* — Melanie Torres Williams
(74) *Attorney, Agent, or Firm* — McDonnell Boehnen Hulbert & Berghoff LLP

(57) ABSTRACT

A spring element for a drug delivery device is proposed, the spring element comprising multiple windings with two windings being mechanically coupled to each other by a rigid transverse connection. Furthermore, a drug delivery device comprising such a spring element and using such a spring element in a drug delivery device are proposed.

14 Claims, 3 Drawing Sheets

(56) References Cited

U.S. PATENT DOCUMENTS 5,137,013 A     8/1992   Chiba et al.
5,180,149 A *   1/1993   Given et al. .................. 267/280
6,878,210 B2 *   4/2005   Tochishita et al. ............ 118/728

OTHER PUBLICATIONS

Lesjofors Group Ed—Stockholm Fjader AB et al: "the spring catalogue" Jan. 1, 1990, Spring Catalogue, Stockholm Fjader AB, SE, XP002145932, figure 6.

* cited by examiner

SPRING ELEMENT FOR A DRUG DELIVERY DEVICE, USE THEREOF AND DRUG DELIVERY DEVICE

CROSS REFERENCE TO RELATED APPLICATIONS

The present application is a U.S. National Phase Application pursuant to 35 U.S.C. §371 of International Application No. PCT/EP2010/054339 filed Mar. 31, 2010, which claims priority to European Patent Application No. 09004663.2 filed on Mar. 31, 2009 and U.S. Provisional Patent Application No. 61/168,980 filed on Apr. 14, 2009. The entire disclosure contents of these applications are herewith incorporated by reference into the present application.

FIELD OF INVENTION

The present disclosure relates to a spring element suitable for use in a drug delivery device, preferably a pen-type injector by which a number of predetermined or user-settable doses of a medical or pharmaceutical product can be administered. In particular, the present disclosure relates to a drug delivery device which can be used by a person without formal medical training, e.g. advanced medical education.

BACKGROUND

Drug delivery devices are in widespread use. For example, they can be applied by persons who do not have a formal medical background. Medical devices can be used to administer accurate and predefined doses of a medical product such as heparin or insulin. In particular, such devices can be used for a healthcare therapy whenever there is demand for a medical or pharmaceutical product being administered on a regular or an irregular basis over a short term or a long term period.

These circumstances set a number of requirements for the drug delivery device of this kind which should be met. The device should be robust in construction, yet easy to use in terms of the manipulations of the parts, easily to be understood by the operator concerning the handling, and/or be suitable for an accurate delivery of the required dose of the medical or pharmaceutical product. Dose setting should be easy and unambiguous. In cases when the device is to be disposable rather than reusable, the device should be cheap to manufacture and easy to dispose of.

SUMMARY

It is an object to provide a reliable spring element for a drug delivery device which should preferably be easy to manufacture.

This object is obtained by a spring element having the features of the independent claim. Advantages embodiments and refinements are subject matter of the dependent claims.

According to a first aspect, a spring element for a drug delivery device comprises multiple windings. At least two of the windings may be, preferably permanently, mechanically coupled to each other by a rigid transverse connection.

Mechanical coupling of at least two consecutive windings by means of the, preferably permanent, rigid transverse connection may enable a reliable spring element. In particular, this enables a reliable propagation of a spring force being exerted by the spring element. At least for the two coupled windings an elastic deformation in a radial direction can be prevented effectively. The term "permanent rigid transverse connection" as used herein, preferably means a rigid transverse connection between consecutive windings which cannot be disconnected and/or shifted to further consecutive windings unless this connection is destroyed by damage.

In a preferred embodiment, the multiple windings are designed such that at least one of the windings is elastically movable with respect to the two windings which are mechanically coupled. This enables reliably propagating the spring force.

According to a further preferred embodiment, the, preferably permanent, rigid transverse connection comprises a material connection. This enables a spring element which is particularly easy to manufacture.

According to a further preferred embodiment, the, preferably permanent, rigid transverse connection comprises a welding. This enables a spring element which is particularly easy to manufacture.

According to a further preferred embodiment, the, preferably permanent, rigid transverse connection is designed such that the two windings are, preferably permanently, coupled by the rigid transverse connection to each other in places.

According to a further preferred embodiment, one of the two windings which are, preferably permanently, mechanically coupled comprises an end winding of the spring element. This enables a reliable spring element by the coupling preventing the end winding of the spring element from moving in a radial direction and/or from sliding over another winding. Thus, a bearing surface of the spring of constant radial extent with or without load on the spring and/or a spring having a reliable spring strength may be provided in a simple manner.

According to a further preferred embodiment, the, preferably permanent, rigid transverse connection is dislocated in regard to a free end of the spring element, in particular an end winding thereof. This enables reducing mechanical tension being exerted on the rigid transverse connection. This may prevent the rigid transverse connection effectively from breakage and therefore may provide a reliable spring element with a long life-time.

According to a further preferred embodiment, more than the two windings are, preferably permanently, mechanically coupled to each other by the rigid transverse connection.

According to a further preferred embodiment, the multiple windings are arranged such that an axial distance between respective consecutive windings varies along the spring element.

According to a further preferred embodiment, two further windings are mechanically coupled to each other by a further, preferably permanent, rigid transverse connection with one of the two further windings comprising a further end winding of the spring element. This enables a reliable production and transportation of the spring element. Additionally, the handling of multiple spring elements is facilitated by reducing the probability that spring elements are hooked with each other, e.g. by a free end of one spring element engaging a winding of another spring element during transportation, storage and/or assembling of the drug delivery device.

According to a further preferred embodiment, the spring element is designed as a coil spring.

According to a further preferred embodiment, the spring element is designed as a pressure spring.

According to a second aspect, a drug delivery device comprises the spring element. The reliable spring element may enable the drug delivery device to become more reliably. The drug delivery device may be a pen-type device.

According to a further embodiment a pen-type device comprises the spring element.

A third aspect relates to using the spring element in a drug delivery device.

According to a preferred embodiment, a spring element for a drug delivery device is provided, the spring element comprising multiple windings with two windings being mechanically coupled to each other by a rigid transverse connection.

BRIEF DESCRIPTION OF THE FIGURES

Further features and refinements become apparent from the following description of the exemplary embodiments in connection with the accompanying figures. The figures illustrate.

DETAILED DESCRIPTION

Figure 1:
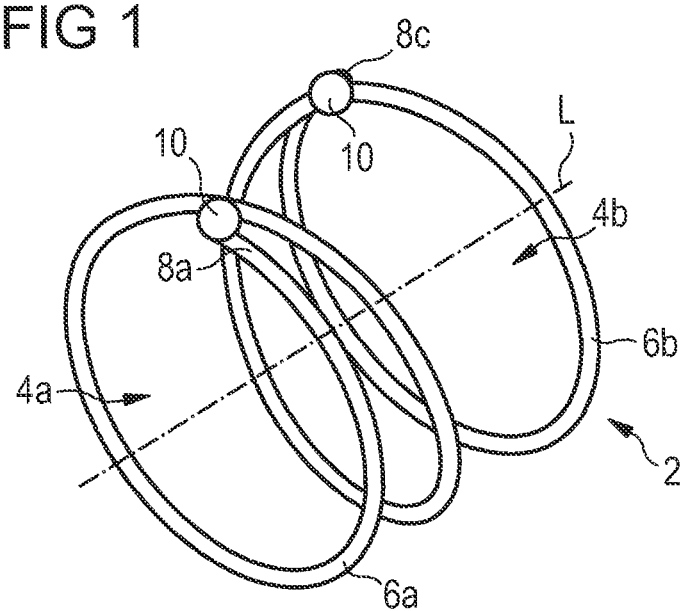
FIG. 1 is a spring element.

Elements of the same design or function are referenced by the same reference numerals in the figures.

FIG. 1 shows a first embodiment of the spring element 2. The spring element 2 has a (main) longitudinal axis L, a first axial end 4a and a second axial end 4b. The (main) longitudinal axis L may extend between the first axial end 4a and the second axial end 4b. The first axial end 4a of the spring element 2 comprises and may, in particular, be formed by a first end winding 6a. The second axial end 4b of the spring element 2 comprises and may, in particular, be formed by a second end winding 6b. The first end winding 6a and the second end winding 6b each comprise a free end 8a and 8b, respectively. Multiple windings, preferably 5 or more, may be present between the two free ends. The respective end winding 6a, 6b may form a respective bearing surface of the spring element 2.

The first end winding 6a is, preferably permanently, connected to, in particular fixed to, a consecutive winding, preferably the immediately consecutive winding, by a rigid transverse connection. The, preferably permanent, rigid transverse connection is arranged at the free end 8a of the first end winding 6a. The rigid transverse connection may cross an intermediate space between two successive windings.

The two windings may be firmly connected by the rigid transverse connection. The consecutive windings may be kept together, in particular joined, by means of the, preferably permanent, rigid transverse connection.

The spring element may be a spring. Preferably, the spring element 2 is designed as a coil spring, particularly preferably as a helical coil spring. The spring element 2 can be, for example, designed as a pressure spring, in particular a pressure coil spring.

In a preferred embodiment, the rigid transverse connection comprises a material connection. For example, the rigid transverse connection can be designed as a welding 10, as it is shown in FIG. 1. For example, the welding 10 can a laser welding. This facilitates a production of a very precise welding 10 by laser welding, particularly if the dimensions of the spring element 2 are very small. Of course, the more precise the welding, the more reliably a constant spring strength may be achieved when fabricating a number of spring elements. However, the rigid material connection may also be a bonding or a soldering.

The rigid transverse connection is expediently designed such that it is non-elastic. This enables a reliable propagation of a spring force by preventing windings of the spring element 2 effectively from being elastically deformed in a radial direction and/or from sliding over a consecutive winding. In a preferred embodiment, as it is shown in FIG. 1, the second axial end 4b of the spring element 2 also comprises a separate rigid transverse connection of the second end winding 6b to a consecutive winding.

Figure 2:
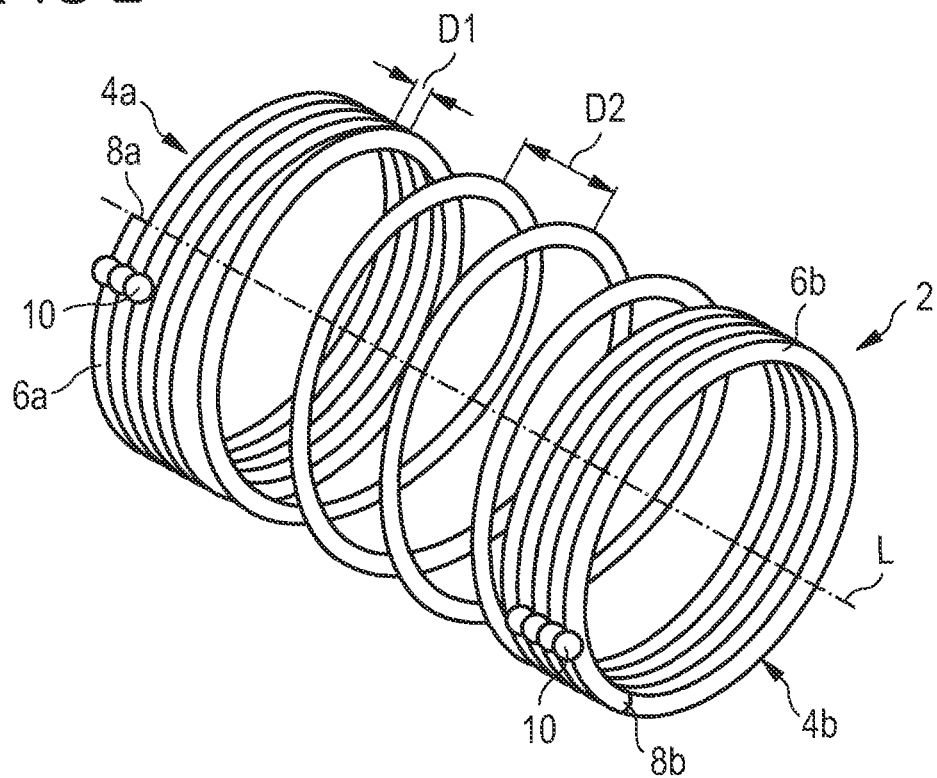
FIG. 2 is a further spring element.

FIG. 2 shows a second embodiment of the spring element 2. The spring element 2 essentially corresponds to the one described in conjunction with FIG. 1.

In contrast thereto, the rigid transverse connection, e.g. a welding 10, couples, preferably permanently, the first end winding 6a and the second end winding 6b rigidly with several consecutive windings, respectively. In a preferred embodiment, an axial distance between consecutive windings varies along the spring element 2. For example, consecutive windings being arranged in the region of the first axial end 4a or of the second axial end 4b of the spring element 2 can be arranged at a first axial distance D1 from each other. Further consecutive windings of the spring element 2, for example windings being arranged in the middle section of the spring element, can be arranged at a further axial distance D2 from each other, where D2 is different from D1, for example D2>D1. This enables a very reliable spring element 2.

If the rigid transverse connection is arranged in a region in which the distance between consecutive windings is small anyway, mechanical load on the rigid material connection may be kept advantageously small. In a preferred embodiment, the respective rigid transverse connection is dislocated in regard to the first free end 8a or the second free end 8b of the respective end winding 6a and 6b. This may further reduce a mechanical tension being exerted on the rigid transverse connection resulting in a reliable spring element 2 having a long lifetime.

Figure 3:
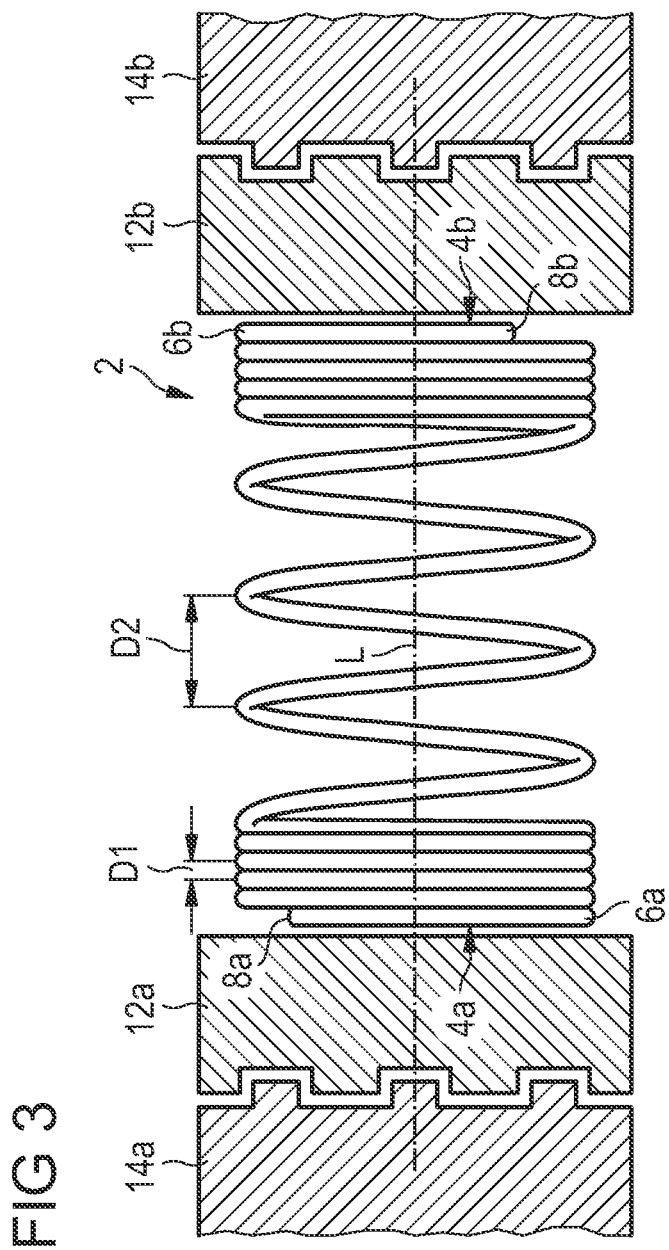
FIG. 3 is the further spring element being arranged between two mechanical clutches.
Figure 4:
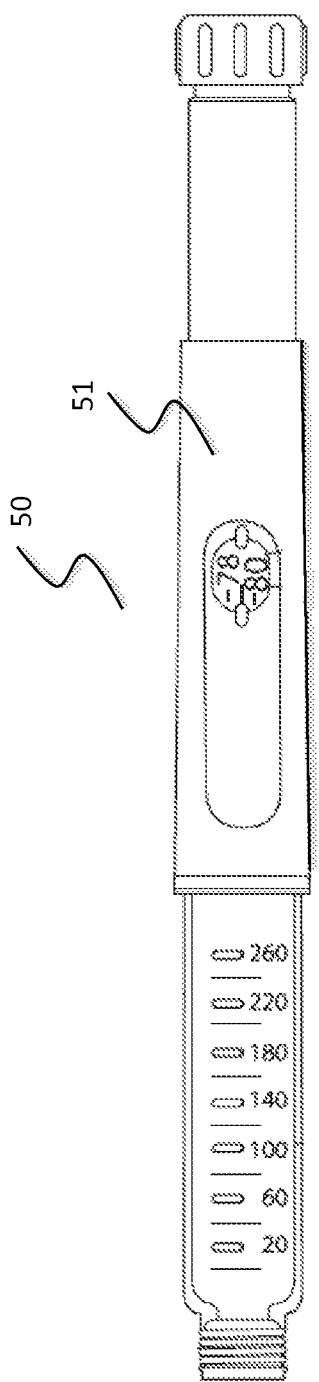
FIG. 4 illustrates one possible drug delivery device of this invention.

FIG. 3 shows the second embodiment of the spring element 2 being provided as a clutch spring for a mechanical clutch. The mechanical clutch is arranged at the first axial end 4a of the spring element 2 and comprises a first clutch member 12a and a second clutch member 14a. The clutch members 12a and 14a are kept in engagement by the spring force exerted by the spring element 2. For example, relative rotational movement of the clutch members may be prevented during engagement. The clutch members 12a and 14a may be parts of a drug delivery device 50, for example a drive mechanism 51 thereof as shown in FIG. 4. The spring element 2 may, therefore, be used as a clutch spring.

A further clutch may be arranged at the second axial end 4b of the spring element 2. The further clutch may comprise a third clutch member 12b and a fourth clutch member 14b. The spring element 2 may keep the clutch members 12b and 14b rotationally locked. Alternatively, the spring element 2 may bear on a simple bearing surface on that side which is remote from the mechanical clutch, i.e. the further clutch may be dispersed with.

Each of the previously shown embodiments of the spring element 2 can be used in a drug delivery device, for example as a clutch spring. The drug delivery device may be a pen-type device. The spring element 2 may be used in a drug delivery device configured for providing an accurate dose of a medical or pharmaceutical product. The term "medical or pharmaceutical product", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A spring element configured as a component part within in a drug delivery device, where the drug delivery device comprises a drive mechanism containing the spring element, the spring element further comprises multiple windings configured for propagating a biasing force inside the drive mechanism of the delivery device, where two of the windings being mechanically coupled to each other by a rigid transverse connection, wherein the multiple windings are arranged such that an axial distance between consecutive windings varies along the spring element and where one of the two windings that are mechanically coupled comprises an end winding of the spring element wherein the rigid transverse connection comprises a welding.

2. The spring element according to claim 1, wherein the multiple windings are designed such that at least one additional winding is elastically movable with respect to the two windings which are mechanically coupled.

3. The spring element according to claim 1, wherein the rigid transverse connection comprises a material connection.

4. The spring element according to claim 1, wherein the rigid transverse connection is designed such that the two windings are coupled by the rigid transverse connection to each other in places.

5. The spring element according to claim 1, wherein the rigid transverse connection is dislocated in regard to a free end of a second end winding.

6. The spring element according to claim 5, wherein the end winding is identical to the second end winding.

7. The according to claim 1, wherein more than the two windings are mechanically coupled to each other by the rigid transverse connection.

8. The spring element according to claim 1, wherein two further windings of the spring element are mechanically coupled to each other by a further rigid transverse connection with one of the two further windings comprising a further end winding of the spring element.

9. The spring element according to claim 1, wherein the spring element is designed as a coil spring.

10. The spring element according to claim 1, wherein the spring element is designed as a pressure spring.

11. A drug delivery device comprising the spring element according to claim 1, wherein the drug delivery device is a pen-type device.

12. The drug delivery device according to claim 11 configured for providing a dose of a medical or pharmaceutical product.

13. A method of using the spring element according to claim 1 in a drug delivery device.

14. A spring element configured to fit and operate as a component part inside a drug delivery device, where the drug delivery device comprises a drive mechanism containing the spring element, the spring element comprising multiple windings configured for propagating a biasing force inside the drive mechanism, where the windings have an end winding being mechanically coupled to a consecutive winding by a rigid transverse connection, wherein the multiple windings are arranged such that an axial distance between consecutive windings varies along the spring element wherein the rigid transverse connection comprises a welding.

* * * * *